United States Patent [19]

Herrera et al.

[11] 4,195,080

[45] Mar. 25, 1980

[54] INSECTICIDAL USE OF ORANGE JUICE ESSENCE OIL

[76] Inventors: Alberto P. Herrera; Sebastian A. Vieto, both of P.O. Box 6614, Panama 5, Panama

[21] Appl. No.: 3,525

[22] Filed: Jan. 15, 1979

Related U.S. Application Data

[63] Continuation of Ser. No. 846,252, Oct. 27, 1977, abandoned.

[51] Int. Cl.$^2$ .............................................. A01N 9/02
[52] U.S. Cl. .................................... 424/186; 424/195
[58] Field of Search ................................ 424/186, 195

[56] References Cited

U.S. PATENT DOCUMENTS 3,303,091   2/1967   Mailander et al. ................... 424/195

OTHER PUBLICATIONS

Chemical Abstracts, vol. 64, (1966), p. 13331a.
Chemical Abstracts, vol. 74, (1971), p. 98434v.
Chemical Abstracts, vol. 74, (1971), p. 41377z.
Guenther, E., "The Essential Oils", vol. 1, (1948), pp. 371, 373, 374.

*Primary Examiner*—V. D. Turner
*Attorney, Agent, or Firm*—Larson, Taylor and Hinds

[57] ABSTRACT

The essence oils of citrus fruit juices, known to be relatively non-toxic to humans, plants and animals, have been found to be lethal insecticides. In addition, the essence oils exhibit a synergistic effect when combined with conventional botanical insecticides such as pyrethrum and the efficiency of the essence oils of citrus fruit juices is increased by the use of a synergist such as technical piperonyl butoxide.

6 Claims, No Drawings

INSECTICIDAL USE OF ORANGE JUICE ESSENCE OIL

This is a continuation, of application Ser. No. 846,252 filed Oct. 27, 1977 (now abandoned).

FIELD OF THE INVENTION

This invention is directed to a method of destroying insects and to insecticidal compositions non-toxic to humans, plants and animals.

BACKGROUND OF THE INVENTION

The number of compounds and materials known today as effective insecticides and pesticides are too numerous to mention. Most of these agents are not without their shortcomings, however, especially in this era of high concern for ecological balance. Responsible governments the world over investigating and prohibiting the use of insecticides and pesticides found to be toxic to humans or which otherwise contribute to an unhealthy environment. In the United States, for instance, the number of pesticides strongly suspected by the Environmental Protection Agency of causing cancer or of otherwise being toxic to man, now totals 100. The agency is continuing its investigations, of 30,000 pesticides currently on the market, to find out which are in fact toxic to humans.

Unfortunately, many of the currently marketed insecticides which have been found to be relatively non-toxic to man, suffer from one or more of the following shortcomings:
1. The lack of effective kill power
2. The lack of an ability to destroy a wide variety of insects.
3. The lack of a persistent or long-lasting kill effect.

Thus, the search for effective insecticides which are non-toxic to humans and which do not have an adverse effect on the environment and ecological conditions continues.

OBJECTS OF THE INVENTION

It is an object of the present invention to provide a method for destroying a wide variety of insects by use of a vegetable substance, non-toxic to man, plants and animals, but lethal to insects.

Another object of the invention is to provide a method for the destruction of insects without adversely effecting the environment or upsetting the ecological balance.

Yet another object of the invention is to provide a method whereby insects are exterminated using an insecticidal composition containing as the active ingredient a vegetable substance found to have a persistent or long-lasting kill effect.

A further object of the invention is to provide a composition having a synergetic effect as an insecticide.

An additional object of the invention is to provide a method of exterminating insects while preserving a healthy environment.

STATEMENT OF THE INVENTION

These and other objects of the invention are achieved by contacting insects with an effective concentration of a composition comprising as the active ingredient citrus juice essence oils. These essence oils are well known by-products of concentrated citrus juice manufacture. The essence oils can be used per se in the method of the invention or in a suitable carrier medium. If desired, the essence oils may be admixed with other coadjuvants including other convention insecticides.

As in another aspect of the invention, it has been surprisingly found that the combination of the essence oils and a botanical insecticide in a weight ratio of about 4:1 to 9:1, preferably 6:1 to 8.5:1, provides a synergestic effect in terms of the lethal power exhibited by the composition against insects.

DETAILED DESCRIPTION OF THE INVENTION

The essence oils employed in the invention are ordinarily obtained from juice extractors during concentration of citrus juice. Generally the oils are obtained from orange and tangerine juices but are also extractable from the juices of lemon, lime, grapefruit, tangelo and murcott. The principle of essence oil recovery from the citrus juice is based on the vaporization of a part (usually about 25%) of the water present in the juices and the tendency of this juice to contain both the oil and the aroma and flavor bearing aqueous components. Concentration and removal of the essence oils is usually obtained by the employment of a stripping column or flash chamber, a reflux column and a chilled product condenser and receiver. In the extraction process, the essence oil floats to the top in the essence phase and is decanted off. Essence oil may also be recovered by extraction from the aqueous phase containing essence oil dissolved therein.

In the United States, essence oils are commonly produced commercially by four different types of recovery units: (1) Atkins, (2) Redd, (3) Walker and (4) Cook. A typical analysis of the physiochemical properties of orange essence oils is as follows:

Physicochemical properties of orange essence oils

| Property | Maximum | Minimum | Average |
|---|---|---|---|
| Sp. grav. 24C/25C | 0.8428 | 0.8403 | 0.8415 |
| Ref. ind.$\eta D^{20}$ | 1.4725 | 1.4721 | 1.4723 |
| Opt. rot. $\alpha D^{25}$ | +99.16 | +97.68 | +98.42 |
| Aldehyde, % | 1.86 | 1.28 | 1.57 |
| Evap. res., % | 1.29 | 0.34 | 0.81 |
| Acid no. | 0.22 | 0.11 | 0.16 |
| Free acid, % | 0.06 | 0.03 | 0.04 |
| Ester no. before acetylation | 3.08 | 2.94 | 3.00 |
| % ester before acetylation | 1.08 | 1.03 | 1.05 |
| Ester no. after acetylation | 6.50 | 5.43 | 6.06 |
| % ester after acetylation | 2.27 | 1.90 | 2.12 |
| Free alcohol, % | 0.97 | 0.64 | 0.84 |
| Total alcohol, % | 1.78 | 1.49 | 1.66 |

The aroma and flavor of essence oils are quite different from other citrus oils having a fruity aroma characteristic of free juice. In addition, the essence oils contain 0.5 to 2.0% valencene, a sesquiterpene not appreciably present in other citrus oils.

While the essence oils may be used per se, i.e. at the 100% strength, such use is unnecessary for the extraordinary insect kill power which characterize the essence oils and enables their use in a highly diluted form. Hence, the essence oils may be introduced as the active ingredient into an inert carrier medium, that is, a medium inert to the essence oil, which carrier medium may take a number of forms. For example, the carrier medium may be either a liquid or a solid. Suitable liquid carriers include water, solvents, preferably organic solvents offensive to insects such as kerosene, alcohols, ketones, ethers, heavy petroleum oils, and aromatic hydrocarbons such as benzene, toluene and xylene. Suitable solid carriers are petrolatum, waxes such as beeswax and other conventional absorbent type carriers which permit the carrying of the essence oils so that they can be dusted or sprayed onto the insects.

It is often advantageous to form emulsions of the essence oils with aqueous or carrier mediums in which the essence oil is relatively insoluble. Any of the conventional emulsifying agents as, for instance, emulsifiers of the "Span," "Triton" or "Tween," series can be employed for this purpose.

The invention also contemplates formulations made up in the form of aerosol sprays. Such formulations generally comprises placing under pressure the necessary components, i.e. the essence oil, with or without other insecticides in a suitable carrier medium and a liquified propellant gas such as carbon dioxide, dichlorofluoromethane and dichlorofluoroethane and the like. In such formulations, the propellant gas will generally constitute 60 to 80% by weight of the total composition.

Thus, the essence oils of the invention may be used per se, as solutions, dispersions and emulsions, or in a solid carrier. When employed in a carrying medium, the concentration of the essence oil can range widely depending principally upon the intended method of application and the nature of the formulation. Generally the concentration of the essence oil in the carrying medium will fall in the range of about 0.01% to 60% by weight.

The other insecticides which may be used in combination with the essence oils of the invention include any of the conventional insecticides such as piperonyl butoxide, methylparathion, malathion, methoxychlor, azinphosmethyl, diazinon and the like. The preferred insecticides for use in combination with the essence oils are the botanical insecticides such as rotenone, nicotine, red squill and pyrethrum. As aforementioned, the botanical insecticides have been unexpectedly found to act synergestically with the essence oils to give an effective kill. This discovery is particulary surprising since the combination of the botanical insectides with other known insecticides fail to exhibit a synergetic effect and do not provide the desired effective kill. In many instances, for example, insects such as certain species of mosquitoes have been found to exhibit a resistance to the insecticides alone or in combination or a strong tendency to recover after contact with the insecticides. In contrast, the combination of essence oil and botanical insecticides shows an extremely lethal effect on insects with little tendency of recovery by the insects.

The insects which can be exterminated by the method and compositions of the present invention include insecticides in that larva, pupal or adult phases such as:

a. Insects which transmit illness: mosquitoes, flys, roaches, bedbugs, fleas, louse, sandflies, triatomas.

b. Insects which damage the agriculture and the cattle: all kinds of insects which affect negatively plants, fruits, cornloft; worms, ticks, etc.

The following specific examples are provides to afford a better understanding of the present invention to those of ordinary skill in the art. It is to be understood that these examples are illustrative only and are not intended to limit the invention in any way.

Example 1 below sets out formulations adapted for particular application according to the present invention.

EXAMPLE I

A. LAVICIDE 1 part orange oil essence
1000 parts water
1% by weight Triton X—100 *1

*1 An emulsifier product of Rohn and Hans comprising isoctyl phenoxy polyethoxy ethanol

B. AEROSOL SPRAY a. Insecticidal Composition:
15% by weight orange essence oil
13.6% by weight
1.4% by weight technical piperonyl butoxide.
b. Inert Ingredients:
70% be weight dichlorofluoroethane as a propellent gas

C. A SPRAY FOR MICRONEBULIZER MACHINES

50% by weight orange essence oil
48.6% by weight kerosene
1.4% by weight technical piperonyl butoxide

D. INSECTICIDAL COMPOSITION FOR USE IN MANUAL OR MECHANICAL SPRINKLERS

25% be weight orange oil essence
74.6% by weight of kerosene
0.4% by weight technical piperonyl butoxide or another adequate insecticide.

EXAMPLE II

The following illustrates a preferred formulation insecticidal composition of the present invention employing a combination of essence oil and a botanical insecticide:

90% by weight orange essence oil
10% by weight pyrethrum; or
97% by weight orange essence oil
0.6% Pyretrum
1% Triton X 100
0.4% Piperonyl Butoxide

EXAMPLE III

One part of the formulation of Example II emulsified in one thousand parts of water with 1% by weight of Triton X-100 provides an effective larvicide.

The following example demonstrates the effectiveness of orange essence oil on the larvas of *Anopheles albimanus* and *Culex pipiens fatigans.*

EXAMPLE IV

In medium enamel trays 33 by 22 cms, were placed the larva of either the *Anopheles albimanus* or the *Culex pipiens fatigans.* To the tray was added the orange essence oil mix in the quanity of water indicated below. The percent of mortality was recorded before 30 minutes had elapsed. The results are summarized in the Tables below.

| Anopheles albimanus | | | |
|---|---|---|---|
| Water Quantity | Qty. of Orange Essence Oil | No. of Larvas | % of mortality |
| 250ml. | 1ml. | 100 | 100 |
| 500ml. | 1ml. | 100 | 100 |
| 750ml. | 1ml. | 100 | 100 |
| 1000ml. | 1ml. | 100 | 100 |
| 1000ml. | Control | 100 | 0 |

After these results were obtained other four tests were realized, using 1 and 2 liters of water with 1 ml. of orange concentrate and 200 larvas, with 100% mortality before 30 minutes had elapsed. There was no mortality in the control.

| Culex pipiens fatigans | | | |
|---|---|---|---|
| Water Quantity | Qty. of Orange Essence Oil | No. of Larvas | % of Mortality |
| 1000ml. | 1ml. | 600 | 95.3 |
| 2000ml. | 1ml. | 600 | 90.0 |
| 2000ml. | Control | 700 | 0 |
| 1000ml. | 2ml. | 200 | 100 |
| 2000ml. | 2ml. | 200 | 100 |
| 2000ml. | Control | 300 | 0 |

EXAMPLE V

From a breeder of Culex pipiens fatigans measuring approximately 13 by 1.4 meters and having a depth of 35 centimeters, were taken ten spoonfuls of medium. Each of the spoonfuls was examined for larva and a positive identification of the presence of both larva and pupas was found in the ten spoonfuls. To the breeder was added one liter of orange essence oil at 100% strength. The results are summarized in the table below.

| BEFORE APPLICATION OF ORANGE ESSENCE OIL | | | |
|---|---|---|---|
| Spoonfuls[*1] Realized | No. of Positive Spoonfuls | Total No. of Larvas | Total No. of Pupas |
| 10 | 10 | 1944 | 30 |

| TWENTY FIVE MINUTES AFTER APPLICATION OF ORANGE ESSENCE OIL | | | |
|---|---|---|---|
| No. of Spoonfuls Realized | No. of Positive Spoonfuls | No. of Larvas | No. of Pupas |
| 10 | 2 | 1 | 1 |

| TWENTY FOUR HOURS AFTER APPLICATION OF ORANGE ESSENCE OIL | | | |
|---|---|---|---|
| No. of Spoonfuls Realized | No. of Positive Spoonfuls | No. of Larvas | No. of Pupas |
| 10 | 4 | 37[*2] | 3 |

[*1] Spoon had 10cms. diameter
[*2] Almost all in the first stage.

As can be seen the data demonstrates clearly the effectiveness of orange essence oil as an insecticide.

The present invention in its broadest aspects is not limited to the specific details shown and described above, but departures may be made from such details without departing from the principles of the invention and without sacrificing its chief advantages.

It is claimed:

1. A method for destroying insects which comprises contacting the insects with effective concentrations of an insecticidal composition comprising as its active ingredient orange juice essence oil obtained by vaporization of orange juice and recovery of the essence oil from the vaporized orange juice.

2. The method of claim 1, wherein the composition includes another insecticide as a coadjutant.

3. The method of claim 2, wherein the other insecticide is a botanical insecticide.

4. The method of claim 3, wherein the botanical insecticide is selected from the group consisting of rotenone, nicotine, red squill and pyrethrum.

5. The method of claim 4, wherein the botanical insecticide is pyrethrum.

6. The method of claim 1, wherein the insects are mosquitoes.

* * * * *